United States Patent
Fujishiro

[11] Patent Number: 5,834,303
[45] Date of Patent: Nov. 10, 1998

[54] METHOD AND DEVICE FOR EXTRACTION AND PURIFICATION OF DNA

[75] Inventor: Masatoshi Fujishiro, Tokyo, Japan

[73] Assignee: Tomy Seiko Co., Ltd., Tokyo, Japan

[21] Appl. No.: 969,688

[22] Filed: Nov. 13, 1997

Related U.S. Application Data

[60] Division of Ser. No. 673,748, Aug. 13, 1996, which is a continuation-in-part of Ser. No. 334,565, Nov. 4, 1994, abandoned.

[51] Int. Cl.[6] .................................................... C12M 3/00
[52] U.S. Cl. ................................... 435/287.7; 435/297.1; 435/304.1; 435/306.1; 210/266; 210/283; 210/287; 210/290
[58] Field of Search ........................... 435/287.7, 297.1, 435/304.1, 306.1; 210/266, 283, 287, 290; 536/25.4, 25.41

[56] References Cited

U.S. PATENT DOCUMENTS

| | | | |
|---|---|---|---|
| 5,329,000 | 7/1994 | Woodard et al. | 536/25.4 |
| 5,330,916 | 7/1994 | Williams et al. | 435/311 |
| 5,342,931 | 8/1994 | Woodard et al. | 536/25.4 |
| 5,405,951 | 4/1995 | Woodard | 536/25.41 |
| 5,438,127 | 8/1995 | Woodard et al. | 536/25.4 |

FOREIGN PATENT DOCUMENTS

| | | |
|---|---|---|
| 04187077 | 7/1992 | Japan . |
| 05252931 | 10/1993 | Japan . |
| WO 93/11218 | 6/1993 | WIPO . |

OTHER PUBLICATIONS

*Preparation and Analytical Purification of DNA from Agarose*, B. Vogelstein et al., Proc. Natl. Acad.Sci.USA, vol. 76, No. 2, pp. 615–619, Feb. 1979.

*A Procedure For the Large–Scale Isolation of Highly Purified Plasmid DNA Using Alkaline Extraction and Binding to Glass Powder*, M. A. Marko et al., Analytical Biochemistry, 121, 1982, pp. 382–387.

*Primary Examiner*—David A. Redding
*Attorney, Agent, or Firm*—Bell Seltzer Intellectual Property Law Group of Alston & Bird LLP

[57] ABSTRACT

A method for the extraction and purification of a plasmid DNA which comprises (1) collecting a culture medium containing a transformant into a first cartridge for the extraction and purification of the DNA, (2) subjecting said transformant to bacteriolysis and RNA degradation conditions, (3) recovering an extract containing solubilized DNA from said first cartridge, (4) transferring said recovered extract to a second cartridge for the extraction and purification of the DNA, and (5) absorbing, washing and eluting purified plasmid DNA from said second cartridge; and a device for the extraction and purification of a DNA which comprises a first cartridge for the extraction and purification of the DNA having at least a trap filter and a membrane filter, and a second cartridge for the extraction and purification of the DNA having at least a glass fiber filter, a glass powder layer and a membrane filter.

11 Claims, 3 Drawing Sheets

Results of agarose gel electrophoresis separation

Lane A : A marker of molecular weight.

Lane B : A plasmid purified by a cesium chloride density gradient centrifugal separation Lane C : A plasmid purified by a method of the present invention

METHOD AND DEVICE FOR EXTRACTION AND PURIFICATION OF DNA

CROSS REFERENCE TO RELATED APPLICATION

This application is a divisional of application Ser. No. 08/673,748, filed Aug. 13, 1996, which is a Continuation in Part of Ser. No. 08/334,565, filed Nov. 4, 1994, now abandoned.

BACKGROUND OF THE INVENTION

The present invention relates to a method and a device for the extraction and purification of a DNA by which the DNA can be extracted and purified in a short period of time from a sample containing many analytes.

Heretofore, in order to extract and purify a plasmid DNA (an extranuclear gene) from a transformant obtained by transforming *E. coli* or the like, a boiling method [Holmes D. S. and M. Quigley, Anal. Biochem., 114, p. 193 (1981)], an alkaline lysis method [Birnboim H. C. and J. Doly, Nucleic Acids Res. 7, p. 1513 (1979)] and the like have been utilized. However, these methods use dangerous reagents such as phenol and chloroform, and they also take much time.

Furthermore, as a method for obtaining a high-purity sample, there is a method for the extraction and purification of a plasmid DNA by a cesium chloride density gradient centrifugal process. This method is a typical technique for the high purification, but in the practice of the method, it takes a long time to complete the method, and the number of samples to be treated at once is only about 10. In addition, equipment in which conventional methods are automated have also been developed, but such equipment are usually expensive and have a drawback that the number of samples to be treated is limited. For these reasons, these equipment are not practical.

The transformation process is one of the fundamental technique in the field of genetic operations, and it is essential to the research and development of life science and biotechnology. Therefore, it has been desired that an extranuclear gene DNA is extracted and purified in a high purity in a short period of time with a high safety from a transformant obtained by this transformation process (in particular, a transformant obtained by transforming *E. coli* or the like).

SUMMARY OF THE INVENTION

Under such circumstances, an object of the present invention is to provide a method and a device for the extraction and purification of an extranuclear gene DNA (a plasmid DNA) by which the DNA duplicated and amplified in a transformant can be inexpensively extracted and purified from an overnight culture medium.

In order to achieve the above-mentioned object, an aspect of the present invention is directed to a method for the extraction and purification of a plasmid DNA which comprises (1) a step of the collection of a culture medium containing a transformant into a first cartridge for the extraction and purification of the DNA, (2) a step of bacteriolysis and the degradation of an unnecessary RNA, (3) a step of impurity filtration by the first cartridge for the extraction and purification of the DNA, and (4) a step of the adsorption, washing and elution of the DNA by a second cartridge for the extraction and purification of the DNA.

In order to achieve the above-mentioned object, another aspect of the present invention is directed to a device for the extraction and purification of a DNA which comprises a first cartridge for the extraction and purification of the DNA having at least a filter for the collection of a transformant and bacteriolysis (hereinafter referred to as "trap filter" in this specification) and a membrane filter, and a second cartridge for the extraction and purification of the DNA having at least a glass fiber filter, a glass powder layer and a membrane filter.

More specifically, the method for the extraction and purification of the DNA regarding the present invention preferably comprises the following steps.

(1) Step of the collection of a transformant culture medium into a first cartridge.

Prior to this step, an overnight culture medium of a transformant is prepared.

Here, a typical example of the transformant to which the present invention can be applied is a transformant obtained by transforming *E. coli* [e.g., *E. coli* JM101 (ATCC 33876), *E. coli* HB101 (ATCC 33694), *E. coli* JM109 (ATCC 53323 or the like] as a host microorganism, but in addition thereto, another transformant of a microorganism as the host to which an alkaline bacteriolysis can be applied can also be used for the extraction and purification of an extranuclear gene DNA.

This transformation can be carried out in accordance with a usual manner known to a person skilled in the art [e.g., Hanahan D., J. Mol. Biol., 166, p. 577 (1983)].

The above-mentioned overnight culture medium is usually prepared by culturing a suitably selected culture medium for several hours.

In the case of the transformant of the *E. coli*, an LB (Luria Bertani) culture medium containing an antibiotic typified by ampicillin is preferable as the selected culture medium in consideration of a drug tolerance gene in a plasmid. In addition thereto, an NZCYM culture medium, an SOC culture medium and the like can also be used. They are not restrictive, and other culture media known to the person skilled in the art can also be used, so long as they do not disturb the achievement of the object of the present invention. That is to say, natural and artificial culture media containing a nitrogen source, a carbon source, a phosphate, a magnesium salt and trace components can be used.

In this step, the thus prepared overnight culture medium is poured into a first cartridge for DNA extraction and purification.

The first cartridge for DNA extraction and purification into which the overnight culture medium has been poured is subjected to a vacuum operation by a vacuum pump or a centrifugal separating operation, thereby collecting the transformant on the first cartridge for DNA extraction and purification. That is to say, the transformant is collected into the steric mesh structure of a trap filter of the first cartridge for DNA extraction and purification.

(2) Step of bacteriolysis and the degradation of an unnecessary RNA.

In this step, a reagent for bacteriolysis is added to the trap filter of the first cartridge for DNA extraction and purification, whereby the transformant is lysed to elute an extranuclear gene (a plasmid DNA) from cells. Furthermore, in this step, an unnecessary RNA are simultaneously digested by the reagent for bacteriolysis.

Therefore, the above-mentioned reagent for bacteriolysis preferably contains a lytic enzyme for the bacteriolysis and a ribonuclease for digesting the RNA. A usable example of the lytic enzyme is lysozyme which is a hydrolase for bacterial cell walls, and a usable example of the ribonuclease is RNase A. The lytic enzyme and the ribonuclease may be each used singly or in a combination of two or more kinds thereof.

As well known, the eluted extranuclear gene (the plasmid DNA) is also utilized as a vector, and the plasmid DNA referred to herein naturally include a cosmid DNA.

This step is carried out by adding the reagent for the bacteriolysis to the trap filter of the first cartridge for DNA extraction and purification, and then allowing the sample to stand at room temperature for 5 to 10 minutes.

(3) Step of impurity filtration by the first cartridge for DNA extraction and purification.

After the end of the above-mentioned step (2), a suitable amount of a reagent for a complete solubilization treatment of the sample, for example, a 0.2N sodium hydroxide.1% sodium lauryl sulfate solution is added onto the trap filter of the first cartridge for DNA extraction and purification, and the sample is then allowed to stand at room temperature for 2 to 5 minutes, whereby the complete solubilization treatment of the sample is achieved.

Next, for example, a suitable amount of 3M potassium acetate (pH=4.8) is added thereto, and the sample is then allowed to stand at room temperature for 3 to 5 minutes. Afterward, the basic solution is neutralized, and a cells-constituting protein and a chromosome DNA are thereby subjected to a solidification treatment.

Afterward, the first cartridge for DNA extraction and purification (into which the culture medium has been first collected) is subjected to a filtrating operation under pressure reduced by a vacuum pump or a filtrating operation by centrifugal separation to separate an extract containing the plasmid DNA (which is extracted through a lower portion of the first cartridge for DNA extraction and purification).

(4) Step of adsorption, washing and elution of the DNA by a second cartridge for DNA extraction and purification.

In this step, the extract obtained in the above-mentioned step (3) and an equal amount of a chaotropic reagent for DNA adsorption, for example, 8M sodium iodide (NaI) are first added to a second cartridge for DNA extraction and purification. This is based on the fact that the adsorption of the DNA onto a glass powder can be accelerated in the presence of chaotropic ions. Furthermore, also in a process in which a DNA fragment separated by agarose gel electrophoresis is extracted from the agarose gel and then purified, the method comprising the DNA adsorption onto the glass powder has been applied [Vogelstein B. and D. Gillespie, Proc. Natl. Acad. Sci., USA, 76, p. 615 (1979)]. Examples of a reagent for producing the chaotropic ions include $LiClO_4$, KI, NaI, NaSCN, LiCl, and $NaCHO_2$, and NaI (sodium iodide) is easily available.

Next, this second cartridge for DNA extraction and purification is subjected to an operation under pressure reduced by a vacuum pump or an operation by centrifugal separation to adsorb the plasmid DNA. This cartridge preferably has an at least four-layer structure comprising glass fiber filters (two layers), a glass powder layer and a membrane filter which will be described hereinafter. The plasmid DNA is mainly adsorbed by the glass powder layer.

Afterward, a buffer solution for washing, for example, 10 mM tris-hydrochloric acid (pH=8.0). 1 mM EDTA.0.2M NaCl.50% ethanol is added to the second cartridge for DNA extraction and purification, and this second cartridge for DNA extraction and purification is then subjected to an operation under pressure reduced by the vacuum pump or an operation by centrifugal separation to carrying out washing.

In the last place, a buffer solution for elution, for example, 50 to 100 $\mu$l of sterilized distilled water/10 mM tris-hydrochloric acid (pH=8.0). 1 mM EDTA is added to the second cartridge for DNA extraction and purification, and this second cartridge for DNA extraction and purification is then subjected to an operation under pressure reduced by the vacuum pump or an operation by centrifugal separation to elute and purify the plasmid DNA alone.

According to the present invention, there are provided a method and a device for the extraction and purification of a DNA by which an extranuclear gene DNA (a plasmid DNA) duplicated and amplified by a transformant can be inexpensively extracted and purified.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Next, a DNA extraction device regarding the present invention will be described with reference to an embodiment shown in attached drawings, and a test example of a DNA extraction method regarding the present invention by the use of this DNA extraction device will be then described. However, as described above, the embodiment and the test example do not intend to limit the technical scope of the present invention, and change, addition and modification within the scope of the technical conception of the present invention are all included in the technical scope of the present invention.

DETAILED DESCRIPTION OF PREFERRED EMBODIMENTS

Figure 1:
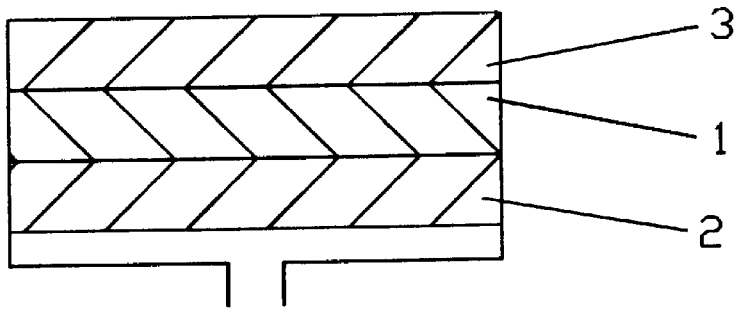
FIG. 1 is a schematic view illustrating the structure of a first cartridge for DNA extraction and. purification.

FIG. 1 shows an embodiment of a first cartridge for DNA extraction and purification of a DNA extraction device regarding the present invention, and in this drawing, reference numeral 1 is a trap filter, numeral 2 is a membrane filter, and 3 is a cartridge container.

The trap filter 1 is mainly a layer for collecting and lysing bacteria such as E. coli which is a transformant. Examples of the preferable material of the trap filter 1 include a glass fiber filter, a polyethylene resin filter and a nonwoven fabric filter, and it preferably has characteristics capable of sterically collecting bacteria such as E. coli. Typically, the glass fiber filter made by Toyo Filter. Paper Co., Ltd. and the polyethylene resin filter made by Spacy Chemical Co., Ltd. can be used.

The membrane filter 2 is mainly a layer for filtering and removing unnecessary substances such as a solidified protein and a chromosome DNA. Examples of the preferable material of the membrane filter 2 include cellulose acetate and polyvinylidene fluoride, and it preferably has characteristics such as biological inertness and low protein absorbability. Typically, the cellulose acetate type membrane filter made by Toyo Filter Paper Co., Ltd. and a durapore membrane made by Millipore Co., Ltd. can be used.

The cartridge container 3 is usually composed of an outer container and a filter fixing inner tube, and the main portion of a cartridge container 3 is usually cylindrical and it has a diameter of 10 to 20 mm and a length of 30 to 50 mm.

In the embodiment shown in FIG. 1, the trap filter 1, the membrane filter 2 and the cartridge container 3 alone are schematically shown, but if necessary, a microtube can be provided. At the time of the use of such a cartridge, necessary peripheral equipment such as a centrifugal machine or a vacuum pump and a cartridge stand for suction can be used, when the present invention is applied.

Figure 2:
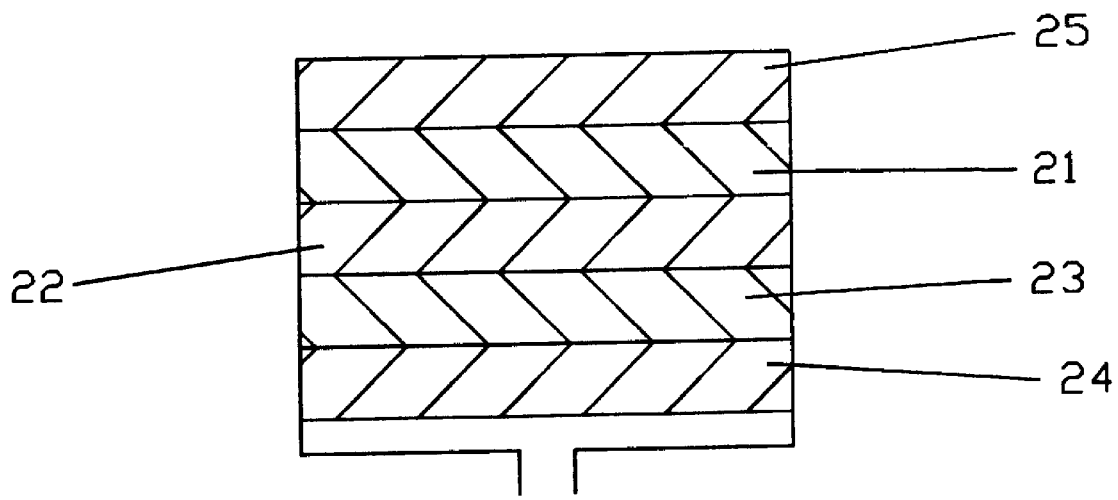
FIG. 2 is a schematic view illustrating the structure of a second cartridge for DNA extraction and purification.

FIG. 2 shows an embodiment of a second cartridge for DNA extraction and purification of the DNA extraction device regarding the present invention, and in this drawing, reference numeral 21 is a glass fiber filter, numeral 22 is a glass powder layer, 23 is a glass fiber filter, 24 is a membrane filter and 25 is a cartridge container.

The glass fiber filters 21 and 23 are mainly layers for the assistance of plasmid adsorption, and at least one such filter is present in the preferred device of the second cartridge. Examples of the preferable material of the glass fiber filters 21 and 23 include fine borosilicate glass fibers, and they preferably have characteristics inert to a biochemical liquid. Typically, GA-100, GA-200 and GC-50 made by Toyo Filter Paper Co., Ltd. and GF series made by Wattman Co., Ltd. can be used.

The glass powder layer 22 is mainly a layer for the DNA adsorption. Its preferable material is a silica matrix or the like, and it preferably has characteristics that its precipitation rate in water is 0.25 cm/minute or less. Typically, a glass powder made by Asahi Glass Co., Ltd. and Glassmilk (trademark) made by Bio 101 Co., Ltd., can be used.

The function and material of the membrane filter 24 and the cartridge container 25 are the same as in the membrane filter 2 and the cartridge container 3 in FIG. 1.

The second cartridge for DNA extraction and purification can be prepared as follows. The glass fiber filter 23 is first superposed upon the membrane filter 24, and 20 to 100 $\mu$l of a glass powder suspension is added onto the glass fiber filter. Next, this cartridge is suctioned under reduced pressure or centrifuged by a swing rotor, whereby the glass powder uniformly adheres onto the glass fiber filter 23, and the glass fiber filter 21 is then laminated thereon to prepare the cartridge having the four-layer structure.

In the embodiment shown in FIG. 2, the glass fiber filter 21, the glass powder layer 22, the glass fiber filter 23, the membrane filter 24 and the cartridge container 25 alone are schematically shown, but if necessary, a microtube for receiving a purified DNA elute can be provided under a cartridge filter. At the time of the use of such a cartridge, necessary peripheral equipment such as a centrifugal machine or a vacuum pump and a cartridge stand for suction can be used, when the present invention is applied.

In general, a glass powder layer is used in the form of suspension. This is due to the fact that a glass powder particle and a molecule of DNA can combine with each other in the presence of a chaotropic ion in the suspension. Consequently, a suspension of a glass powder is utilized in the preparation of the glass powder layer. The linking phenomenon between glass powder particles and molecules of DNA tend to be adversely affected if the suspension of the glass powders is allowed to dry out. It seems that the decrease of the surface area of glass powder caused by aggregation among the glass powder particles results in a decrease in the total number of links.

Figure 4:
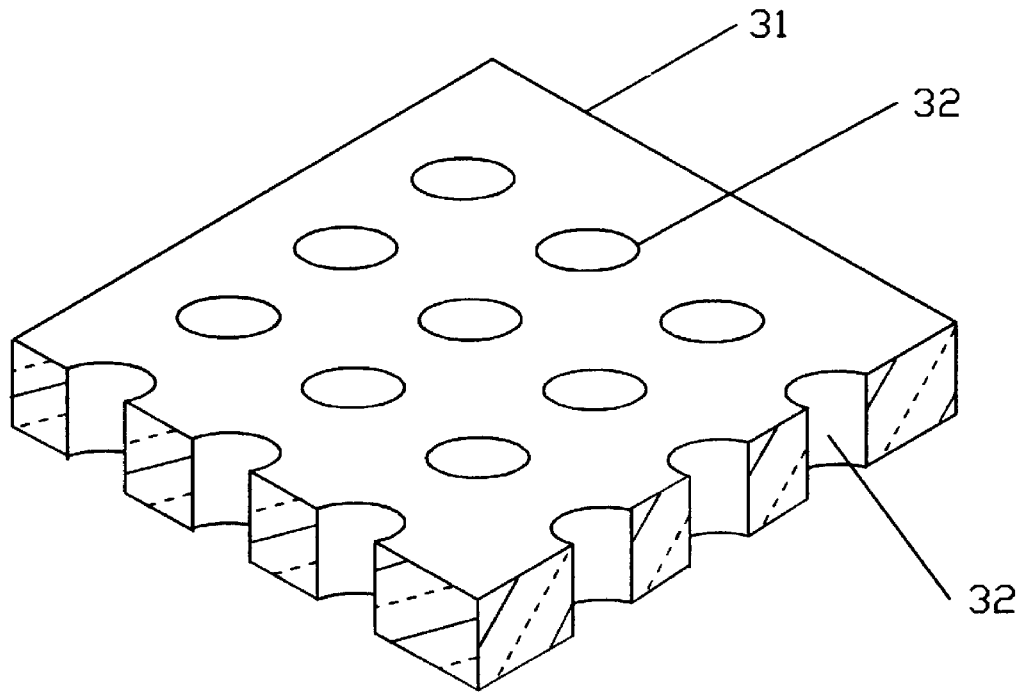
FIG. 4 is a schematic view illustrating a specific embodiment of the glass powder layer of a second cartridge for DNA extraction and purification.
Figure 5:
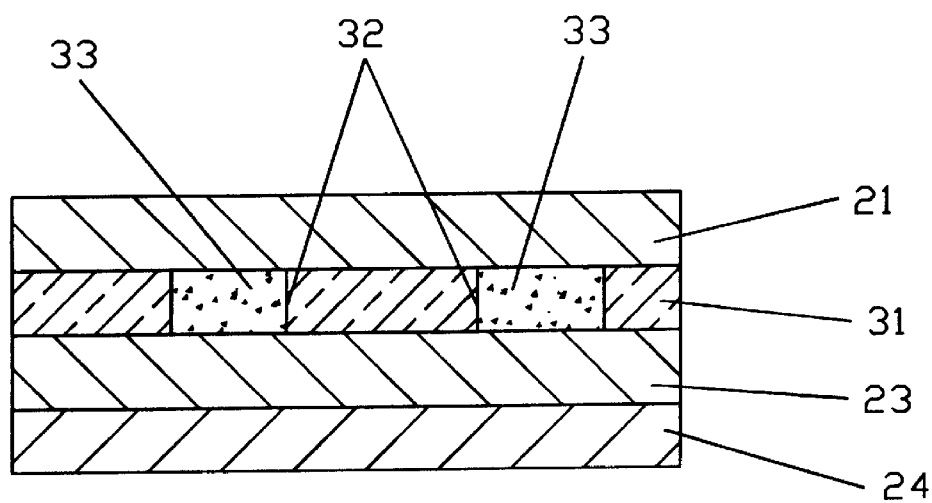
FIG. 5 is a schematic view illustrating in detail a specific embodiment of the four layer structure of a second cartridge for DNA extraction and purification.

To prevent a glass powder layer from drying, the present invention provides a use of a new type of a glass powder layer as illustrated in FIG. 4 and FIG. 5.

Referring to FIG. 4, there is provided a perforated structure comprising a sheet 31 of substantially impervious material containing a plurality of holes 32. This perforated structure is applied in place of the glass powder layer 22 of the embodiment of the present invention, illustrated in FIG. 2. The sheet 31 is positioned on glass fiber filter 23 and is preferably adhered to the glass fiber filter by ultrasonic welding or other suitable means. Then, a suitable amount of a dry glass powder is filled in holes 32. Finally, sheet 31 is preferably covered by and adhered to the other glass fiber filter 21. FIG. 5 is a sectional view of the four layer laminate structure thus obtained. The functions and advantages of this structure are basically identical to those of the four layer structure described above. Because the glass powder layer according to FIG. 4 and 5 is prepared in a dry state, and the suspension of glass powder is formed only upon or immediately prior to use, the glass powder sheet is storage stable and could be used more than six months after preparation.

The number of the holes in the sheet of FIG. 4 is preferably about 200 to 300 holes over an area of 300 mm×300 mm. The diameter of each of the holes is preferably about 6 to 8 mm. The amount of the glass powder filled into each of the holes is preferably about 30 to 50 mg. Sheet 31 of FIG. 4 and FIG. 5 is suitably PVC, polyethylene, polypropylene or the like, and may also be constructed of other moisture resistant material such as certain papers. The thickness of sheet 31 is preferably from about 0.5 to 1.0 mm.

The materials constituting the respective layers of the first and second cartridges for DNA extraction and purification can be inexpensively formed or obtained from a market. Therefore, the device of the present invention can be provided at a low manufacturing cost.

Next, reference will be made to a test example of a method for the extraction and purification of a DNA regarding the present invention by the use of the first and second cartridges for DNA extraction and purification shown in FIGS. 1 and 2.

Test Example (1) Step of the collection of a transformant culture medium into a first cartridge.

Prior to this step, an overnight culture medium of a transformant was prepared.

As a host microorganism, there was used a transformant obtained by transforming E. coli HB101 (ATCC 33694) in accordance with a Hanahan method [Hanahan D., J. Mol. Biol., 166, p. 577 (1983)].

As a selected culture medium, a Luria Bertani culture medium containing ampicillin was used.

The composition of this culture medium was as follows:

Bacto-tryptone 10 g/l

Bacto-yeast extract 5 g/l

NaCl 10 g/l

Ampicillin 35–50 mg/l

The pH of the culture medium was adjusted to 7.5 with sodium hydroxide.

3 ml. of this culture medium was cultured overnight.

In the case of using the first and second cartridges for DNA extraction and purification shown in FIGS. 1 and 2, the amount of the culture medium was preferably in the range of 1 to 3 ml.

The thus prepared overnight culture medium was poured into the first cartridge for DNA extraction and purification.

The first cartridge for DNA extraction and purification into which the overnight culture medium had been poured was subjected to a centrifugal separating operation, whereby the transformant was collected into a trap filter of the first cartridge for DNA extraction and purification.

(2) Step of bacteriolysis and the degradation of an unnecessary RNA.

200 µl of a reagent for bacteriolysis was added to the trap filter of the first cartridge for DNA extraction and purification to lyse the transformant, thereby eluting an extranuclear gene (a plasmid DNA) from cells. Furthermore, in this step, an unnecessary RNA was simultaneously digested by the reagent for bacteriolysis.

In the reagent used for bacteriolysis, lysozyme was contained as a lytic enzyme and RNase A was contained as a ribonuclease.

In this step, the reagent for bacteriolysis was added to the trap filter of the first cartridge for DNA extraction and purification, and it was then allowed to stand at room temperature for 10 minutes.

(3) Step of impurity filtration by the first cartridge for DNA extraction and purification.

After the above-mentioned step (2), as a reagent for a complete solubilization treatment of the sample, 400 µl of a 0.2N sodium hydroxide.1% sodium lauryl sulfate solution was added onto the trap filter of the first cartridge for DNA extraction and purification, and it was then allowed to stand at room temperature for 5 minutes, whereby the complete solubilization treatment of the sample was achieved.

Next, 300 µl of 3M potassium acetate (pH=4.8) was added thereto, and the sample was then allowed to stand at room temperature for 5 minutes. Afterward, the basic solution was neutralized, and a cells-constituting protein and a chromosome DNA were thereby insolubilized by a solidification treatment.

Afterward, the first cartridge for DNA extraction and purification (into which the culture medium had been first collected) was subjected to a filtrating operation by centrifugal separation to separate an extract containing the plasmid DNA (which was extracted through a lower portion of the first cartridge for DNA extraction and purification).

(4) Step of adsorption, washing and elution of the DNA by a second cartridge for DNA extraction and purification.

In this step, the extract obtained in the above-mentioned step (3) and an equal amount of 8M sodium iodide NaI as a reagent for DNA adsorption were first added to a second cartridge for DNA extraction and purification.

Next, this second cartridge for DNA extraction and purification was subjected to a centrifugal separating operation, whereby the plasmid DNA was adsorbed on a glass fiber filter and a glass powder of this cartridge.

Furthermore, as a buffer solution for washing, 350 µl of 10 mM tris-hydrochloric acid (pH=8.0).1 mM EDTA.0.2M NaCl.50% ethanol was added to this second cartridge for DNA extraction and purification, and the second cartridge was then subjected to a centrifugal separating operation to carry out washing.

In the last place, as a buffer solution for elution, 100 µl of distilled water 10/mM tris-hydrochloric acid (pH=8.0).1 mM EDTA was added to this second cartridge for DNA extraction and purification, and the second cartridge was subjected to a centrifugal separating operation to elute and purify the plasmid DNA alone.

Figure 3:
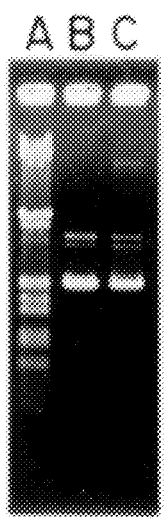
FIG. 3 is a graph showing the results of electrophororesis in a test example.

FIG. 3 shows the results of the agarose gel electrophoresis separation of the plasmid DNA purified in the above-mentioned test example. The presence of a RNA, a DNA derived from a chromosome, and a protein which were impurities was not observed at all, and there could be obtained the plasmid DNA having a purity equal to or higher than a plasmid DNA purified by a cesium chloride density gradient ultracentrifugal separation process. Therefore, it was confirmed that the thus obtained plasmid DNA could be used in various analysis experiments without any problem.

In the practice of the present invention using the four layer structure of FIG. 5 in the second cartridge, the procedures to be followed are substantially the same as described above. In a preferred method, a suitable solution of a chaotropic agent is added to the second cartridge prior to adding the extract from the first cartridge in order to wet the glass fiber filters and glass powder, although this step is not essential. For example, in a preferred method, the glass fiber filters and glass powder are first contacted with 500 µl of a solution of 10M sodium thiocyanate. Thereafter, the extract from the first cartridge is added, followed by an additional 1000 µl of the 10M NaSCN solution. Thereafter, the second cartridge is washed and purified plasmid DNA eluted as previously described.

The invention being thus described, it will be obvious that the same may be varied in many ways. Such variations are not to be regarded as a departure, from the spirit and scope of the invention, and all such modifications as would be obvious to one skilled in the art are intended to be included within the scope of the following claims.

That which is claimed is:

1. A device for the extraction and purification of plasmid DNA from a culture medium containing a transformant which comprises:

a first cartridge comprising a trap filter and a membrane filter and means for extracting solubilized plasmid DNA through said membrane filter, and a second cartridge comprising at least one glass fiber filter, a glass powder layer and a membrane filter, and means for extracting solubilized plasmid DNA through said membrane filter.

2. A device of claim 1 wherein said means for extracting said solubilized DNA through said membrane filter comprises a connector for applying a vacuum to the extraction side of said filter.

3. A device of claim 1 wherein said glass powder layer of said second cartridge is positioned between two glass fiber filters.

4. A device of claim 1 wherein said glass powder layer comprises a sheet of substantially impervious material having a plurality of holes containing said glass powder.

5. A device of claim 4 wherein said sheet is positioned between two glass fiber filters.

6. A device of claim 5 wherein said sheet is adhered to at least one of said glass fiber filters.

7. A device of claim 4 wherein said glass powder contained in the holes of said sheet is in a dry condition.

8. A device of claim 4 wherein said sheet contains from about 200 to 300 holes per 300 mm×300 mm area and said holes are from about 6 mm to 8 mm in diameter.

9. A device of claim 8 wherein each hole contains from about 30 mg to 50 mg of glass powder.

10. A device of claim 4 wherein said sheet is plastic.

11. A kit for the extraction and purification of plasmid DNA from a culture medium containing a transformant which comprises:

a first cartridge comprising a trap filter and a membrane filter with inlet means for adding a culture medium to said trap filter and outlet means for extracting solubilized materials through said membrane filter, and a second cartridge comprising at least one glass fiber filter, a glass powder layer and a membrane filter with inlet means for adding the extract from said first cartridge to said glass fiber filter and outlet means for extracting solubilized materials through said membrane filter.

* * * * *